(12) United States Patent
Tsuchimoto et al.

(10) Patent No.: US 10,588,522 B2
(45) Date of Patent: Mar. 17, 2020

(54) BIOLOGICAL SENSOR

(71) Applicant: Murata Manufacturing Co., Ltd., Nagaokakyo-shi, Kyoto-fu (JP)

(72) Inventors: Hirofumi Tsuchimoto, Nagaokakyo (JP); Takanori Hayashi, Nagaokakyo (JP); Kengo Saito, Nagaokakyo (JP); Hiroyuki Nakaji, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 422 days.

(21) Appl. No.: 15/012,958

(22) Filed: Feb. 2, 2016

(65) Prior Publication Data

US 2016/0143549 A1 May 26, 2016

Related U.S. Application Data

(63) Continuation of application No. PCT/JP2014/070317, filed on Aug. 1, 2014.

(30) Foreign Application Priority Data

Aug. 7, 2013 (JP) ................................. 2013-164150

(51) Int. Cl.
*A61B 5/024* (2006.01)
*A61B 5/00* (2006.01)
*A61B 5/1455* (2006.01)

(52) U.S. Cl.
CPC ...... *A61B 5/02427* (2013.01); *A61B 5/02416* (2013.01); *A61B 5/14552* (2013.01);
(Continued)

(58) Field of Classification Search
CPC ... A61B 5/0261; A61B 5/7264; A61B 5/0095; A61B 5/02427; A61B 5/1455;
(Continued)

(56) References Cited

U.S. PATENT DOCUMENTS 5,259,381 A * 11/1993 Cheung .............. A61B 5/02427
356/41
5,355,882 A 10/1994 Ukawa et al.

FOREIGN PATENT DOCUMENTS

JP H02-13815 A 1/1990
JP H06-22943 A 2/1994
(Continued)

OTHER PUBLICATIONS

"Wireless Dictionary", 2005, Althos Publishing, First Printing, p. 70.*

(Continued)

*Primary Examiner* — Deborah L Malamud
(74) *Attorney, Agent, or Firm* — Arent Fox LLP

(57) ABSTRACT

A biological sensor capable of improving the signal to noise ratio of a detection signal obtained by a light-receiving element and amplified by an amplifier is provided.

The biological sensor includes a microcontroller that generates a driving signal, a light-emitting element that emits light in accordance with the driving signal, a light-receiving element that outputs a current detection signal based on an intensity of received light, and an amplifying circuit that converts the current detection signal into a voltage detection signal, amplifies an alternating current component of the voltage detection signal, and outputs an amplified detection signal. Furthermore, the microcontroller generates an offset signal that is applied to an offset circuit to offset the direct current component of the voltage detection signal and to obtain biological information by processing the amplified detection signal.

8 Claims, 9 Drawing Sheets

(52) U.S. Cl.
CPC .......... *A61B 5/7203* (2013.01); *A61B 5/7228* (2013.01); *A61B 2562/0238* (2013.01)

(58) Field of Classification Search
CPC ............ A61B 5/486; A61B 2562/0233; A61B 5262/0238; A61B 5/0245; A61N 2005/0659; A61N 2005/067; A61N 2005/0661; A61N 2005/0663; A61N 2005/0656; A61N 5/06; A61N 1/08; A61N 1/36125; A61N 2005/0662; F21K 9/00

See application file for complete search history.

(56) References Cited

FOREIGN PATENT DOCUMENTS

| | | |
|---|---|---|
| JP | H06-63024 A | 3/1994 |
| JP | H11-253414 A | 9/1999 |
| JP | 2007-105133 A | 4/2007 |

OTHER PUBLICATIONS

Sclater, Neil et al, "McGraw-Hill Electronics Dictionary", 1997, McGraw-Hill, Inc., Sixth Edition, pp. 455-456.*
"The IEEE Standard Dictionary of Electrical and Electronics Terms", 1996, Standards Coordinaring Committee 10, Sixth Edition, pp. 1074-1075.*
Laplante, Phillip A., "Comprehensive Dictionary of Electrical Engineering", 1999 CRC Press LLC, p. 57.*
International Search Report issued for PCT/JP2014/070317, dated Nov. 4, 2014.
Written Opinion of the International Searching Authority issued for PCT/JP2014/070317, dated Nov. 4, 2014.

\* cited by examiner

OUTPUT CURRENT OF LIGHT-RECEIVING ELEMENT 20
(a)
(b)
TIME

OFFSET VOLTAGE
(c)
(d)
TIME

OUTPUT VOLTAGE OF AMPLIFYING UNIT 30
(e)
TIME

PRIOR ART

PRIOR ART

BIOLOGICAL SENSOR

CROSS REFERENCE TO RELATED APPLICATION

The present application is a continuation of PCT/JP2014/070317 filed Aug. 1, 2014, which claims priority to Japanese Patent Application No. 2013-164150, filed Aug. 7, 2013, the entire contents of each of which are incorporated herein by reference.

FIELD OF THE INVENTION

The present invention relates to biological sensors that detect biological information.

BACKGROUND

Conventional photoplethysmographic sensor, pulse oximeters, and the like that obtain, as photoplethysmographic signals, changes in the intensity of light that passes through a biological body such as a finger or is reflected by the biological body by exploiting the characteristics of blood hemoglobin that absorb visible light to infrared light are known (see Patent Document 1, for example).

Here, the pulse oximeter according to Patent Document 1 includes first and second light-emitting diodes that are driven in an alternating manner by pulse signals outputted from an oscillation circuit so as to irradiate biological tissue with red light and infrared light, and a photodiode that detects a light output after the stated light has been absorbed by the biological tissue. Light reception output from the photodiode is amplified by an amplifier, and is then distributed and inputted to a computing unit in synchronization with the output of the oscillation circuit using a multiplexer. Based on direct current components and pulsation components in respective wave lengths obtained from the light reception output of the photodiode, the computing unit calculates a percentage $\Phi$ of the pulsation components of absorbance of an artery blood flow, and then calculates an arterial blood oxygen saturation from the percentage $\Phi$ of the pulsation components of the absorbance.

Patent Document 1: Japanese Patent No. 3116252.

Incidentally, external light from sources aside from the light-emitting diodes (a light-emitting element) (sunlight, fluorescent lamp light, or the like, for example) sometimes enters into the photodiode (a light-receiving element). There is a risk that such external light will combine with the light originally to be detected, namely the light that has passed through the biological body or that has been reflected by the biological body, and lead to a drop in the signal to noise ratio of the detection signal.

According to the pulse oximeter of Patent Document 1, when external light has entered the light-receiving element in such a combined manner and the external light component (a DC noise component) has increased, the amplifier output is saturated and the pulsation component (a signal component) can no longer be accurately extracted. However, if the amplification rate of the amplifier is reduced to prevent the output saturation, the amplitude of the pulsation component will also drop, resulting in a risk that the accuracy of detecting the oxygen saturation will drop. In the case where the signal is encoded including the external DC noise component, it will be necessary for the resolution of an A/D converter to be sufficiently high with respect to the pulsation component, which leads to an increase in costs. What is needed, therefore, is a technique that enables an improvement in the signal to noise ratio of a detection signal obtained when a light-receiving element receives light and the resulting signal is amplified by an amplifier.

SUMMARY OF THE INVENTION

Having been conceived to solve the aforementioned problems, it is an object of the present invention to provide a biological sensor capable of improving the signal to noise ratio of a detection signal obtained when a light-receiving element receives light and the resulting signal is amplified by an amplifier.

A biological sensor according to the present invention includes a microcontroller including driving signal generating unit that generates a driving signal; a light-emitting element that emits light in accordance with the driving signal; a light-receiving element that outputs a current detection signal based on an intensity of received light; and an amplifying circuit that converts the current detection signal into a voltage detection signal, amplifies an alternating current component of the voltage detection signal, and outputs an amplified detection signal. The microcontroller further includes an offset unit that offsets the direct current component of the voltage detection signal; and is configured to obtain biological information by processing the amplified detection signal.

According to the biological sensor of the present invention, the voltage detection signal when the detected current signal is converted into the voltage detection signal and amplified is offset. Through this, the ratio of an alternating current signal component can be increased by reducing a direct current component caused by DC noise produced by external light or the like. Accordingly, the amplification rate, which has conventionally been reduced in order to prevent saturation caused by direct current component noise, can be set higher. As such, the signal to noise ratio of the detection signal obtained by the light-receiving element and amplified by the amplifying circuit can be improved.

In the biological sensor according to the present invention, it is preferable that the driving signal generating unit generates a pulse-form driving signal, and the offset unit generates and applies a pulse-form offset voltage synchronized with the pulse-form driving signal generated by the driving signal generating unit.

In this case, the light-emitting element is driven in a blinking manner by the pulse-form driving signal, and thus the amount of power consumed thereby can be reduced as compared to a case where the light-emitting element is constantly on. Furthermore, the pulse-form offset voltage synchronized with the pulse-form driving signal is applied to the amplifying circuit, and thus the DC noise component can be cut from the detection signal obtained by the light-receiving element when the light-emitting element is on.

In the biological sensor according to the present invention, the amplifying circuit includes a first operational amplifier that converts the current detection signal into the voltage detection signal, a second operational amplifier that amplifies the voltage detection signal to output the amplified detection signal, and a capacitor connected between an output terminal of the first operational amplifier and an input terminal of the second operational amplifier; and the offset unit applies the offset voltage to a path between the output terminal of the first operational amplifier and the input terminal of the second operational amplifier.

In this case, the offset voltage can be applied using a typical amplifying circuit constituted by the two-stage combination of the operational amplifiers, and thus the amplifying circuit can be realized at a low cost. Furthermore, employing a configuration in which the offset voltage is applied to the path between the output terminal of the first operational amplifier and the capacitor makes it possible to relax range setting requirements for the first operational amplifier, which in turn makes it possible to increase the degree of freedom of design.

In the biological sensor according to the present invention, it is preferable that the offset unit of the microcontroller includes an offset signal generating unit that generates an offset signal, and a voltage dividing circuit that includes a plurality of resistors and that generates the offset voltage by voltage-dividing the offset signal generated by the offset signal generating unit.

In this case, using the offset signal generating unit and the voltage dividing circuit in combination with each other makes it possible to improve the accuracy of the offset voltage applied to the amplifier. Accordingly, the DC noise component can be cut with accuracy.

Preferably, the biological sensor according to the present invention further includes a light-emitting element that outputs light of a different wave length from the light-emitting element; the driving signal generating unit generates pulse-form driving signals having mutually different timings for each of the plurality of light-emitting elements; the offset unit generates pulse-form offset voltages independent from each other in synchronization with the respective pulse-form driving signals outputted at mutually different timings, and applies the offset voltages.

According to this configuration, the pulsed light outputted from the plurality of light-emitting elements can be received by the single light-receiving element. The DC noise component can be cut from each instance of the light outputted from the plurality of light-emitting elements at mutually different wave lengths. Accordingly, the signal to noise ratio can be improved for each instance of the pulsed light outputted from the plurality of light-emitting elements.

The biological sensor according to the present invention, the microcontroller further includes a direct current component extracting circuit that extracts a direct current component of the amplified detection signal, and an offset voltage determining unit that determines the offset voltage outputted by the offset unit so that a deviation of the direct current component extracted by the direct current component extracting circuit from a target value decreases.

In this case, the offset voltage is determined dynamically, and thus measurement robustness can be ensured by appropriately cutting the DC noise component even in the presence of variations caused by individual differences in the measurement subject's (subject's) skin state, thickness, diameter, and so on, seasonal changes in the skin state, differences in measurement areas, and so on, or fluctuations in signal levels due to body movement. Furthermore, the offset voltage range can be continually in use in a closed-loop circuit; as such, it is not necessary to set a gain margin in consideration of the stated variations or body movement, and the pulse and oxygen saturation measurement can consistently be carried out at the maximum gain setting.

In the biological sensor according to the present invention, it is preferable that operations of the microcontroller including generating the driving signal and generating the offset signal can be stopped when the deviation does not become less than or equal to a predetermined value as a result of the offset voltage determined by the offset voltage determining unit.

In this case, the measurement is ended in the case where the measurement could not be correctly taken due to the influence of external light or the like, which makes it possible for a user such as a subject to easily recognize the success or failure of the measurement, and prompts the user to take correct measurements using the biological sensor.

According to the present invention, the signal to noise ratio of a detection signal obtained by a light-receiving element and amplified by an amplifier can be improved.

DETAILED DESCRIPTION

Figure 1:
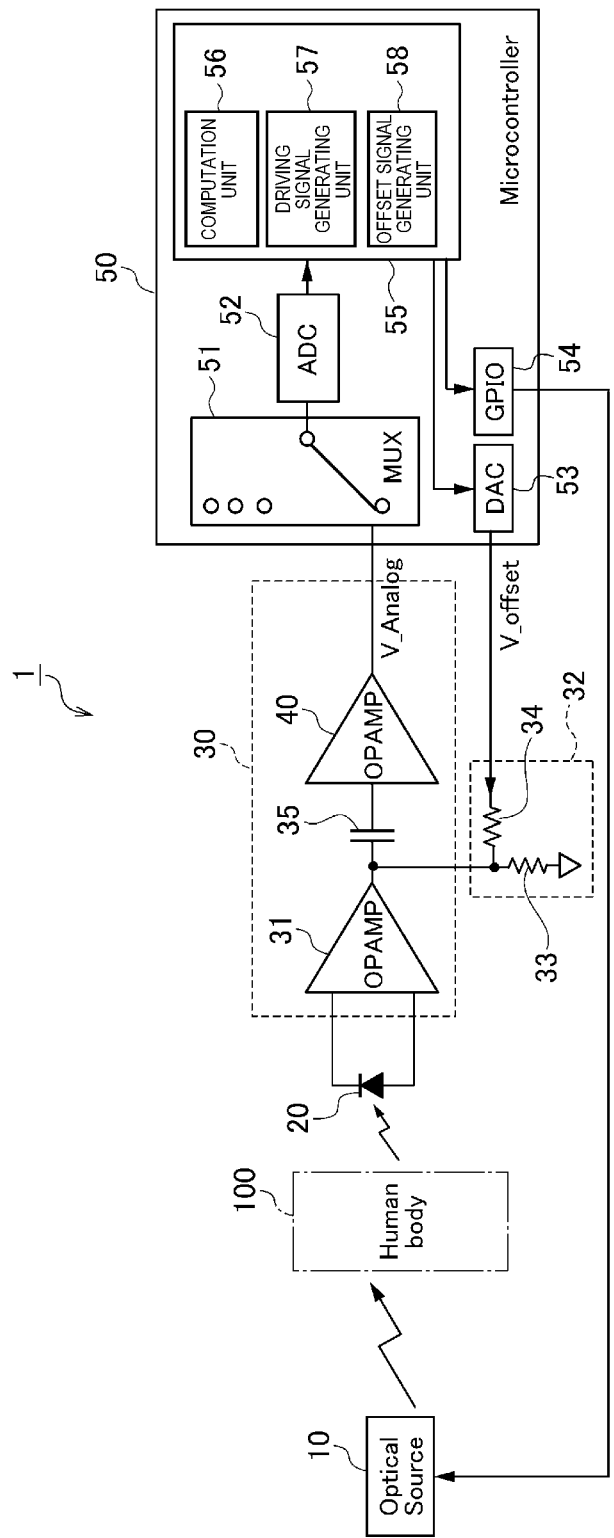
FIG. 1 is a block diagram illustrating the configuration of a biological sensor according to a first embodiment.

Hereinafter, preferred embodiments of the present invention will be described in detail with reference to the drawings. In the drawings, the same reference numerals are used for identical or corresponding portions. Furthermore, the same reference numerals are appended to identical elements and redundant descriptions thereof will be omitted.

First Embodiment

Figure 2:
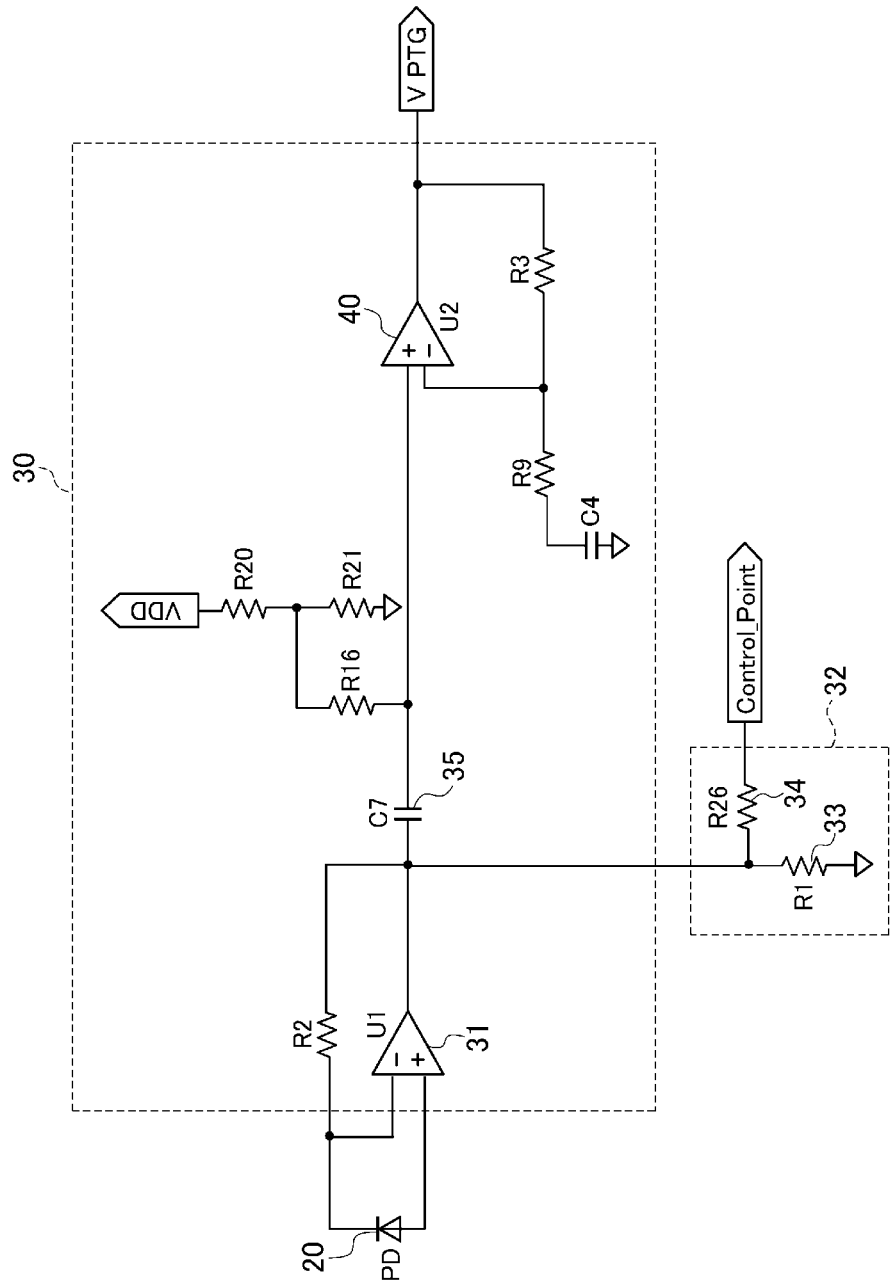
FIG. 2 is a circuit diagram illustrating an input section that constitutes the biological sensor according to the first embodiment.

First, the configuration of a biological sensor 1 according to a first embodiment will be described with reference to FIGS. 1 and 2. Here, FIG. 1 is a block diagram illustrating the configuration of the biological sensor 1. FIG. 2, meanwhile, is a circuit diagram illustrating an input section that constitutes the biological sensor 1.

The biological sensor 1 is a sensor that uses light absorption characteristics of blood hemoglobin to optically detect a photoplethysmographic signal and measure biological information such as a pulse, for example. As such, the biological sensor 1 is primarily configured of a light-emitting element 10, a light-receiving element 20, an amplifying unit 30, a microcontroller 50, and so on. The amplifying unit 30 corresponds to an amplifying circuit as described herein.

The light-emitting element 10 emits light based on a pulse-shaped driving signal outputted from an output port 54 of the microcontroller 50. For example, an LED, a VCSEL (Vertical Cavity Surface Emitting LASER), a resonator-type LED, or the like can be used as the light-emitting element 10. Note that a 600 Hz pulse signal is used as the driving signal in the exemplary embodiment, but should in no way be so limited to this frequency.

The light-receiving element 20 outputs a detection signal (also called a "detection current signal" or "photoplethysmographic signal" hereinafter) based on the intensity of incident light that has been emitted from the light-emitting element 10 and then passed through a human body 100 such as a fingertip or reflected by the human body 100. For example, a photodiode, a phototransistor, or the like can be preferably used as the light-receiving element 20. A photodiode is used as the light-receiving element 20 in the exemplary embodiment. The light-receiving element (photodiode) 20 is connected to the amplifying unit 30, and the detection signal obtained by the light-receiving element (photodiode) 20 is outputted to the amplifying unit 30.

The amplifying unit 30 includes two operational amplifiers 31 and 40 connected in multiple stages (two stages, in the exemplary embodiment), and amplifies the detection signal outputted from the light-receiving element (photodiode) 20.

More specifically, a cathode electrode of the photodiode 20 is connected to an inverting input (−) terminal of the operational amplifier 31 in the former stage (a first stage) (called a "first operational amplifier" hereinafter). Meanwhile, an anode terminal of the photodiode 20 is connected to a non-inverting input (+) terminal of the first operational amplifier 31. A voltage dividing resistor group 32 (corresponding to a voltage dividing circuit as described herein) that divides an analog signal outputted from a D/A converter 53 of the microcontroller 50 and applies the resulting signal is connected to an output terminal of the first operational amplifier 31.

More specifically, the voltage dividing resistor group 32 includes a first resistor 33 whose one end is connected to the output terminal of the first operational amplifier 31 and one end of a capacitor 35 and whose other end is connected to a ground, and a second resistor 34 whose one end is connected to the one end of the first resistor 33 and whose other end is connected to an output terminal of the D/A converter 53. Accordingly, a voltage obtained by dividing the analog signal outputted from the D/A converter 53 in accordance with a ratio between the resistance value of the first resistor 33 and the resistance value of the second resistor 34 (also called an "offset voltage" or a "correction voltage" hereinafter) appears at the connection point between the first resistor 33 and the second resistor 34 (in other words, at the output terminal of the first operational amplifier 31 and the one end of the capacitor 35). Accordingly, an output potential of the first operational amplifier 31 when a current detection signal from the photodiode 20 is transformed into a voltage detection signal and amplified is offset by the offset voltage.

An output terminal of the first operational amplifier 31 is connected to an input terminal (a non-inverting input (+) terminal) of the second operational amplifier 40 through a capacitor 35 (in other words, AC-coupling). A detection signal amplified by the first operational amplifier 31 (also called a "voltage detection signal" or a "photoplethysmographic signal" hereinafter) has its direct current component removed by the capacitor 35, and is amplified again by the subsequent (the second stage) operational amplifier (called the "second operational amplifier" hereinafter) 40. An output terminal of the second operational amplifier 40 is connected to the microcontroller 50, and the amplified detection signal is outputted to the microcontroller 50.

The microcontroller 50 obtains biological information such as the pulse of a user by processing the detection signal (also called an "amplified detection signal" or "photoplethysmographic signal" hereinafter) detected by the photodiode 20 and amplified by the amplifying unit 30. The microcontroller 50 also outputs a driving signal to the light-emitting element 10 and outputs the offset signal to the voltage dividing resistor group 32. Accordingly, the microcontroller 50 is configured so as to include a multiplexer 51 and an A/D converter 52 serving as an input interface, a CPU 55 that carries out computational processes on a detection signal inputted through the A/D converter 52, a ROM that stores programs and data for causing the CPU to execute various processes, a RAM that temporarily stores various types of data such as computational results, the D/A converter 53 that outputs the offset signal (analog signal), the output port 54 that outputs the driving signal, and so on.

As shown, the microcontroller 50 includes a plurality of units including a computation unit 56, a driving signal generating unit 57, and an offset signal generating unit 58 by the CPU 55 executing programs stored in the ROM. It should be appreciated that when each of these units is described herein, it is contemplated that the microcontroller is configured to execute the described algorithms for such corresponding units. Further, it is noted that the A/D converter 52, the D/A converter 53, the CPU 55, the ROM, the RAM, and so on may be constituted by independent chips according to one exemplary embodiment.

The multiplexer 51 selects and switches between input ports for A/D conversion. The multiplexer 51 switches between input ports based on a control signal from the CPU. The detection signal (photoplethysmographic signal) from the input port selected by the multiplexer 51 is sent to the A/D converter 52.

The A/D converter 52 converts the detection signal (photoplethysmographic signal) from the input port selected by the multiplexer 51 into digital data at a predetermined sampling period. The digitized detection signal is outputted to the computation unit 56.

The computation unit 56 obtains the biological information such as a pulse by processing the obtained detection signal (photoplethysmographic signal). In other words, the computation unit 56 functions as a computing processor as described herein. Note that the obtained biological information such as a pulse is outputted to the exterior or stored in the aforementioned RAM or the like.

The driving signal generating unit 57 generates a pulse-form driving signal for driving the light-emitting element 10, and outputs the driving signal through the output port 54. The driving signal generating unit 57 is set to generate a pulse wave having a frequency of 600 Hz as the driving signal in the exemplary embodiment.

The offset signal generating unit 58 generates a pulse-form offset signal (digital data) synchronized with the pulse-form driving signal outputted by the driving signal generating unit 57, based on a division ratio in the voltage dividing resistor group 32. For example, in the case where an offset voltage of 3.0 (V) is to be applied to the first operational amplifier 31, and the division ratio of the voltage dividing resistor group 32 is set to ⅔, for example, the offset signal (analog data) is generated so that 4.5 (V) is outputted from the D/A converter 53. Note that the configuration may be such that the voltage dividing resistor group 32 is omitted and the output of the D/A converter 53 is connected directly to the output terminal of the first operational amplifier 31.

The offset signal (digital data) generated by the offset signal generating unit 58 is converted into an analog signal by the D/A converter 53 and is then outputted to the voltage dividing resistor group 32. In other words, the offset signal generating unit 58, the D/A converter 53, and the voltage dividing resistor group 32 function as an offset unit or offset circuit as described herein.

By employing the aforementioned configuration, in the biological sensor 1 according to the exemplary embodiment, a pulse signal having a frequency of 600 Hz, for example, is generated by the driving signal generating unit 57 of the microcontroller 50 and outputted from the output port 54. The light-emitting element 10 to which the pulse signal is applied emits pulsed light at a predetermined wave length based on the pulse signal. The pulsed light that is emitted from the light-emitting element 10 and that passes through the human body 100 such as a fingertip or is reflected by the human body 100 then enters the light-receiving element 20 and is converted into a current signal (current detection signal) by the light-receiving element 20.

Meanwhile, the offset signal generating unit 58 of the microcontroller 50 generates the pulse-form offset signal (digital data) that is synchronized with the pulse signal (driving signal). The offset signal is converted into an analog voltage by the D/A converter 53 and is applied to the voltage dividing resistor group 32. Accordingly, the voltage (offset voltage) obtained by the voltage division in accordance with the ratio between the resistance value of the first resistor 33 and the resistance value of the second resistor 34 that constitute the voltage dividing resistor group 32 is applied to the output of the first operational amplifier 31.

Figure 3:
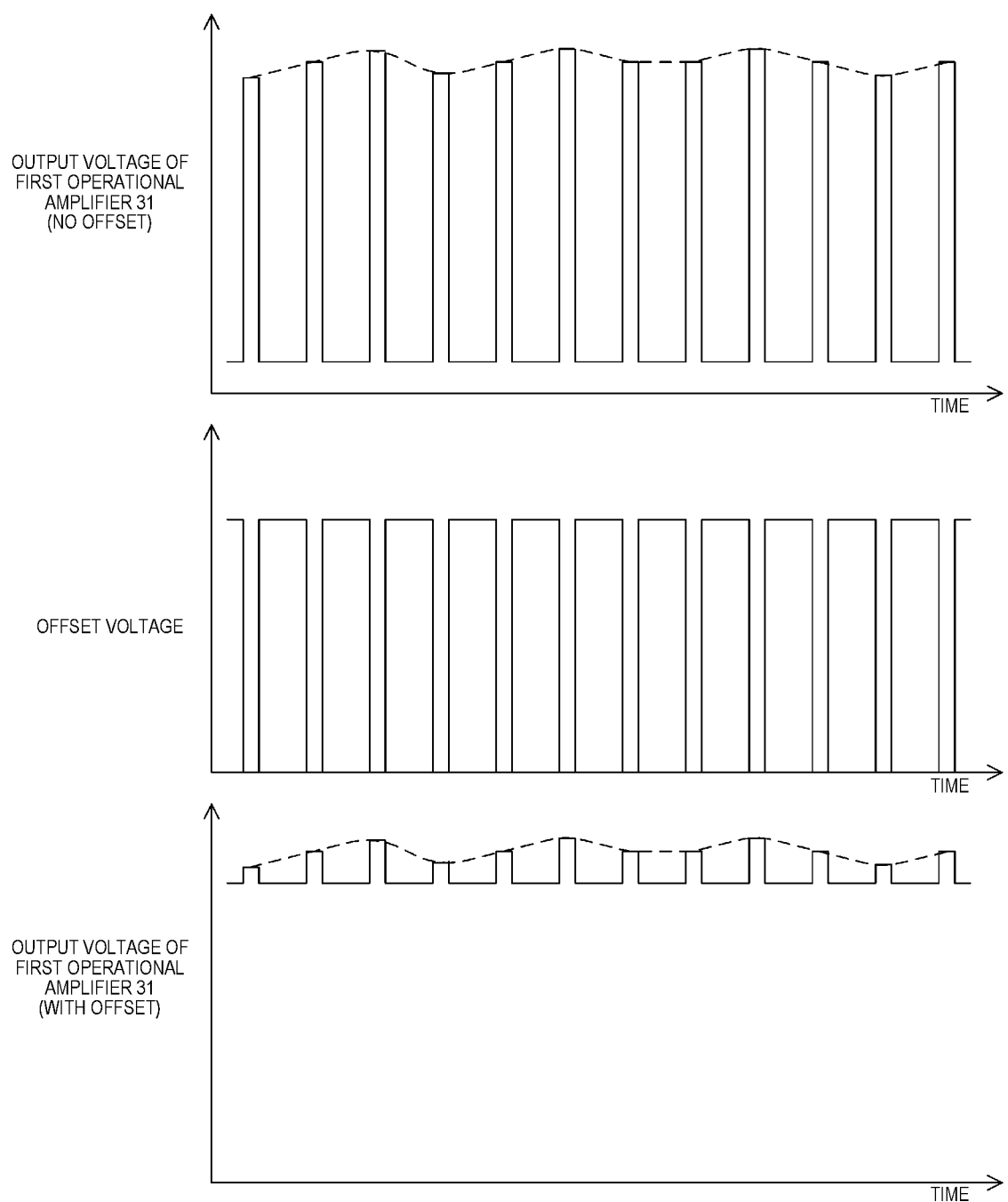
FIG. 3 is a diagram illustrating an offset voltage according to the first embodiment.

An effect achieved in the case where the offset voltage is applied to the output of the first operational amplifier 31 will be described using FIG. 3. The upper section of FIG. 3 illustrates an output voltage (voltage detection signal) after I-V conversion by the first operational amplifier 31, in the case where the offset voltage is not applied. As illustrated in FIG. 3, a square wave voltage detection signal having an amplitude equivalent to an appropriate percent of a dynamic range is outputted from the first operational amplifier 31 in synchronization with the driving pulse of the light-emitting element 10. The middle section of FIG. 3 illustrates an offset voltage signal. The exemplary embodiment assumes that the offset voltage signal is added to the voltage detection signal. The offset voltage has a waveform with a constant peak value inverse from the voltage detection signal, and has an amplitude approximately equivalent to the direct current component (base line) of an envelope connecting the peaks of the voltage detection signal (the broken line in the upper graph). The lower section of FIG. 3 illustrates the output voltage of the first operational amplifier 31 that has been offset, obtained by adding the output voltage in the upper section and the offset voltage in the middle section. The direct current component of the output voltage illustrated in the lower section is cut by the capacitor 35 and the resulting signal is inputted into the second operational amplifier 40. The voltage detection signal amplified by the first operational amplifier 31 and offset in this manner is inputted into the microcontroller 50 after being further amplified by the subsequent second operational amplifier 40.

Here, when S represents a signal component voltage, N represents a DC noise component voltage, G1 represents a conversion gain in the I-V conversion performed by the first operational amplifier 31, G2 represents a voltage gain in the second operational amplifier 40, and Vo represents the offset voltage, an output signal waveform from the amplifying unit 30 is defined as ((S+N)×G1−Vo)×G2. As such, according to the exemplary embodiment, (S+N)×G1×G2 (and G2 in particular) can be increased by −Vo×G2 as compared to the case where no offset is applied, which makes it possible to improve the signal to noise ratio in the signal outputted from the amplifying unit 30.

The amplified detection signal inputted into the microcontroller 50 is supplied to the computation unit 56 through the multiplexer 51 and the A/D converter 52. The detection signal is then processed by the computation unit 56, and the biological information such as a pulse is obtained.

According to the exemplary embodiment as described thus far, the output potential of the first operational amplifier 31 when the detection signal is amplified is offset. Accordingly, the output potential of the amplifier when converting the detected current signal into a voltage signal is offset. Through this, the ratio of an alternating current signal component can be increased by reducing a direct current component caused by noise produced by external light or the like. Accordingly, the amplification rate, which has conventionally been reduced in order to prevent saturation caused by direct current component noise, can be set higher. As such, the signal to noise ratio of the detection signal obtained by the light-receiving element 20 and amplified by the amplifying unit 30 (the second operational amplifier 40) can be improved. As a result, a range in which no pulse is detected, based on individual differences from measurement subject to measurement subject, can be reduced. In other words, the detection rate can be improved. In addition, low-noise requirements for the amplifying unit 30 can be relaxed, which makes it possible to reduce the cost of the circuit components of which the amplifying unit 30 is configured. Furthermore, the offset voltage can be applied using a typical amplifying configuration constituted by the two-stage combination of the operational amplifiers 31 and 40, and thus the amplifying unit 30 can be realized at a low cost. Furthermore, the resolution of the A/D converter 52 can be lowered, which makes it possible to achieve even lower costs.

In addition, according to the exemplary embodiment, the light-emitting element 10 is driven in a blinking manner by the pulse-form driving signal, and thus the amount of power consumed thereby can be reduced as compared to a case where the light-emitting element 10 is constantly on. Furthermore, the pulse-form offset voltage synchronized with the pulse-form driving signal is applied to the first operational amplifier 31, and thus the DC noise component can be cut from the detection signal obtained by the light-receiving element 20 when the light-emitting element 10 is on.

Furthermore, according to the exemplary embodiment, the offset voltage can be accurately generated and applied by using the combination of the D/A converter 53 and the voltage dividing resistor group 32, in cases such as where the resolution would be insufficient if only the D/A converter 53 was used, for example. Accordingly, the DC noise component can be cut with accuracy.

The signal to noise ratio improvement effects obtained by applying the offset voltage to the output of the first operational amplifier 31 were confirmed by simulating the analog output voltage outputted from the amplifying unit 30, for both a case where the offset voltage is applied to the output of the first operational amplifier 31 (the exemplary embodiment) and a case where the offset voltage is not applied (a conventional circuit; a comparative example). The signal to noise ratio improvement effect obtained by applying the offset voltage to the output of the first operational amplifier 31 will be described next with reference to FIGS. 4 to 6.

Figure 4:
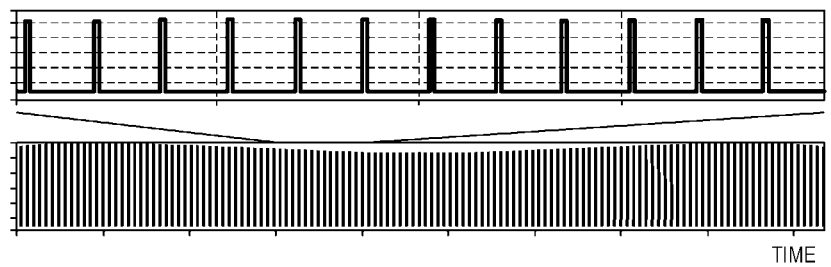
FIG. 4 is a diagram illustrating results of a simulation of an output voltage and the like outputted from an amplifying unit of the biological sensor according to the first embodiment.
Figure 4:
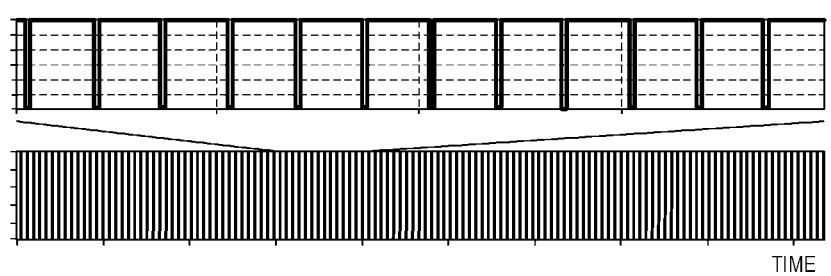
Figure 4:
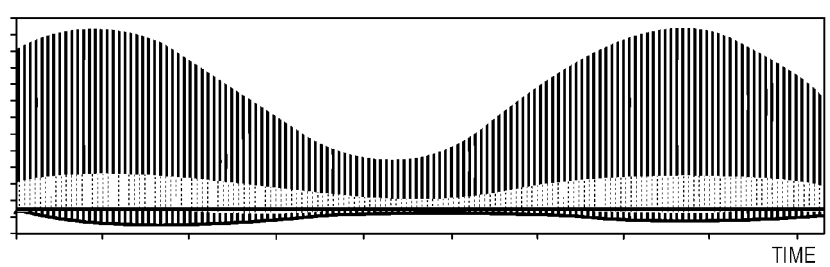
Figure 5:
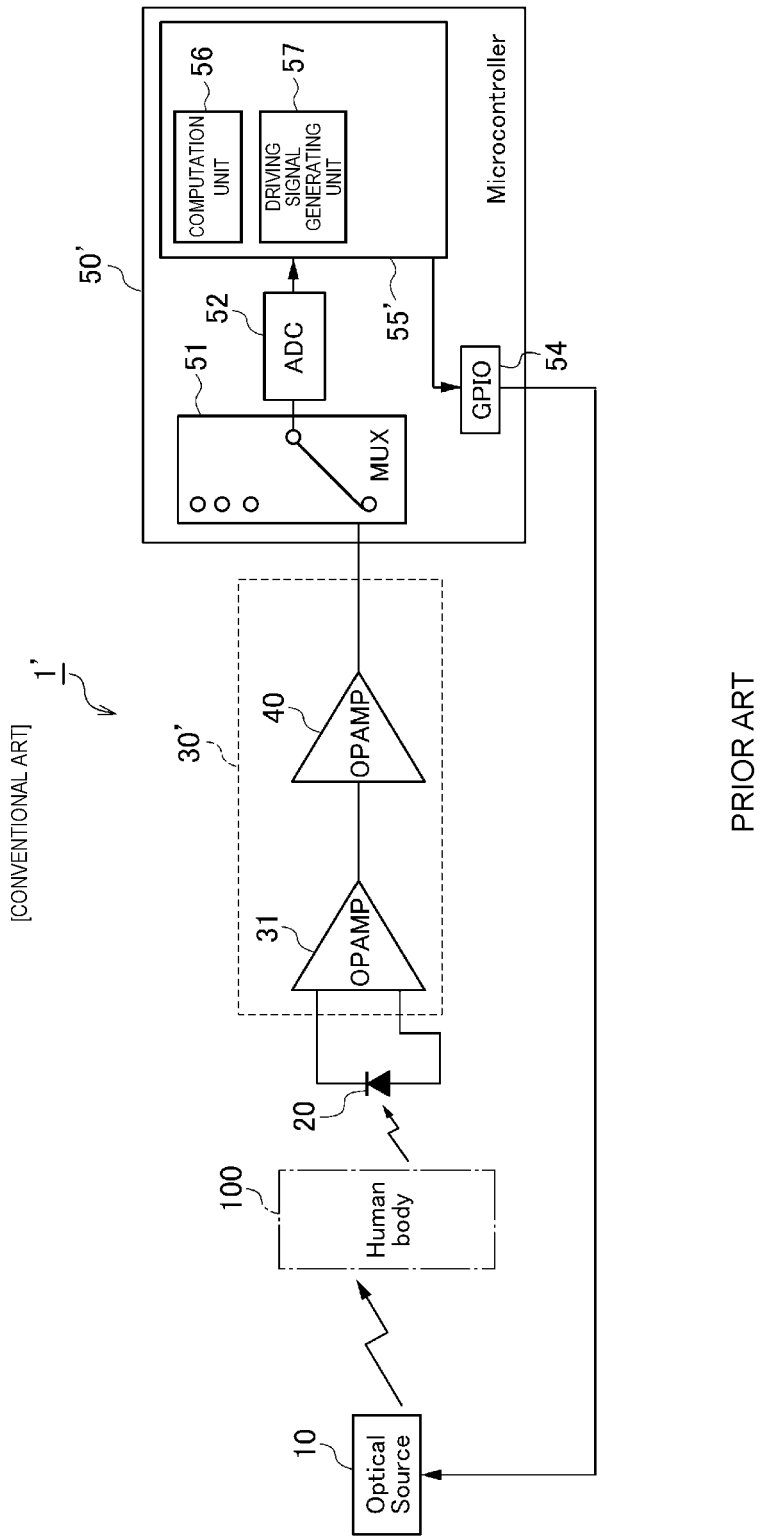
FIG. 5 is a block diagram illustrating the configuration of a biological sensor according to a conventional technique (a comparative example).
Figure 6:
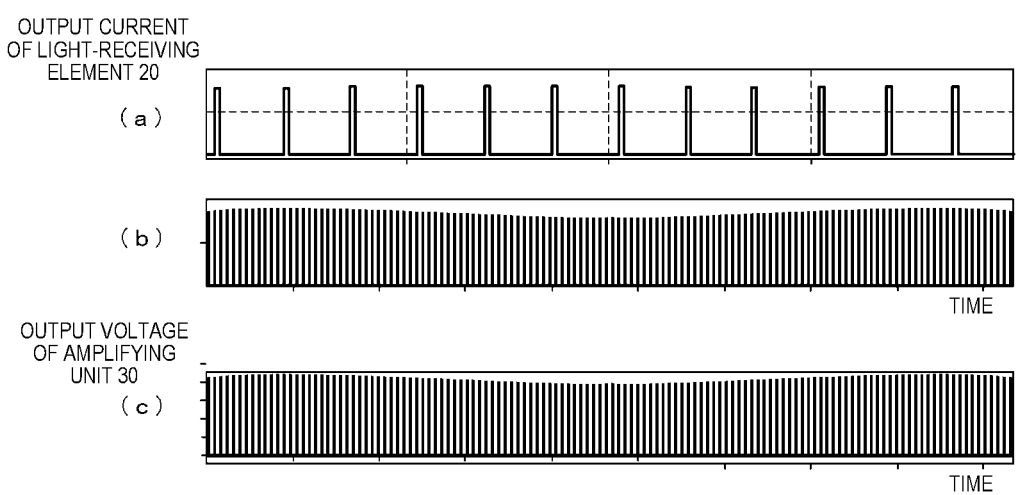
FIG. 6 is a diagram illustrating results of a simulation of an output voltage and the like outputted from an amplifying unit of the biological sensor according to the conventional technique (the comparative example).

FIG. 4 is a diagram illustrating results of a simulation of the detection signal outputted from the amplifying unit 30 of the biological sensor 1 according to the exemplary embodiment. FIG. 5 is a block diagram illustrating the configuration of a biological sensor 1' according to a conventional technique, used as a comparative example. FIG. 6, meanwhile, is a diagram illustrating results of a simulation of an output voltage outputted from an amplifying unit 30' of the biological sensor 1' according to the conventional technique (comparative example) illustrated in FIG. 5.

First, the result of simulating the output voltage outputted from the amplifying unit 30 of the biological sensor 1 according to the exemplary embodiment will be described with reference to FIG. 4. In FIG. 4, graph (b) indicates the output current from the light-receiving element 20, graph (a) indicates a waveform obtained by expanding the output current from the light-receiving element 20 indicated in graph (b) along the time axis, graph (d) indicates the offset voltage, graph (c) indicates a waveform obtained by expanding the offset voltage indicated in graph (d) along the time axis, and graph (e) indicates the analog output voltage from the amplifying unit 30 (the second operational amplifier 40). The horizontal axes in FIG. 4 represent time.

The amplitude (0–p) of the offset voltage in graphs (c) and (d) of FIG. 4 was 3 V. In the analog output voltage indicated by the dotted line area in graph (e), an amplitude (p–p) corresponding to DC noise (N) was 0.5 V and an amplitude corresponding to a signal (S) (a pulse amplitude) was 0.34 V. Accordingly, the signal to noise ratio was 0.34/0.5, or in other words, approximately 68%, thus confirming that the signal to noise ratio can be improved as compared to the conventional circuit, which will be described later.

A waveform obtained in the case where the amplification rate of the amplifying unit 30 was set to 3,125,000× is indicated by a solid line area in graph (e) of FIG. 4. In this case, as indicated by the solid line area in graph (e), it was confirmed that the amplitude of the pulse wave signal could be set to 12,500,000× without degrading the pulse wave signal (detection signal) and without saturating the pulse wave signal.

Next, the results of simulating the output voltage (pulse wave signal) outputted from the amplifying unit 30' of the biological sensor according to the conventional circuit (comparative example) will be described with reference to FIGS. 5 and 6. As described above, FIG. 5 is a block diagram illustrating the configuration of the biological sensor 1' employing the conventional circuit, used as a comparative example. As illustrated in FIG. 5, this biological sensor 1' does not include the offset signal generating unit 58, the D/A converter 53, or the voltage dividing resistor group 32. Accordingly, the offset voltage that offsets the output voltage is not applied to the first operational amplifier 31 that constitutes the amplifying unit 30'.

FIG. 6 illustrates a result of simulating the output voltage outputted from the amplifying unit 30' of the biological sensor 1' in the conventional circuit (comparative example) illustrated in FIG. 5. In FIG. 6, graph (b) indicates the output current from the light-receiving element 20, graph (a) indicates a waveform obtained by expanding the output current from the light-receiving element 20 indicated in graph (b) along the time axis, and graph (c) indicates the analog output voltage from the amplifying unit 30' (the second operational amplifier 40). The horizontal axes in FIG. 6 represent time.

In the case where the offset voltage is not applied when I-V converting and amplifying the light-receiving current indicated in graph (a) of FIG. 6, the amplitude (p–p) corresponding to the DC noise (N) was 2.5 V and the amplitude corresponding to the signal (S) (the pulse amplitude) was 0.34 V in the analog output voltage indicated in graph (c). The signal to noise ratio was thus 0.34/2.5, or in other words, approximately 13.6%.

Based on the aforementioned results, it was confirmed that the biological sensor 1 according to the exemplary embodiment can improve the signal to noise ratio from approximately 13.6%, of the biological sensor 1' according to the conventional circuit, to approximately 68%.

Second Embodiment

Figure 7:
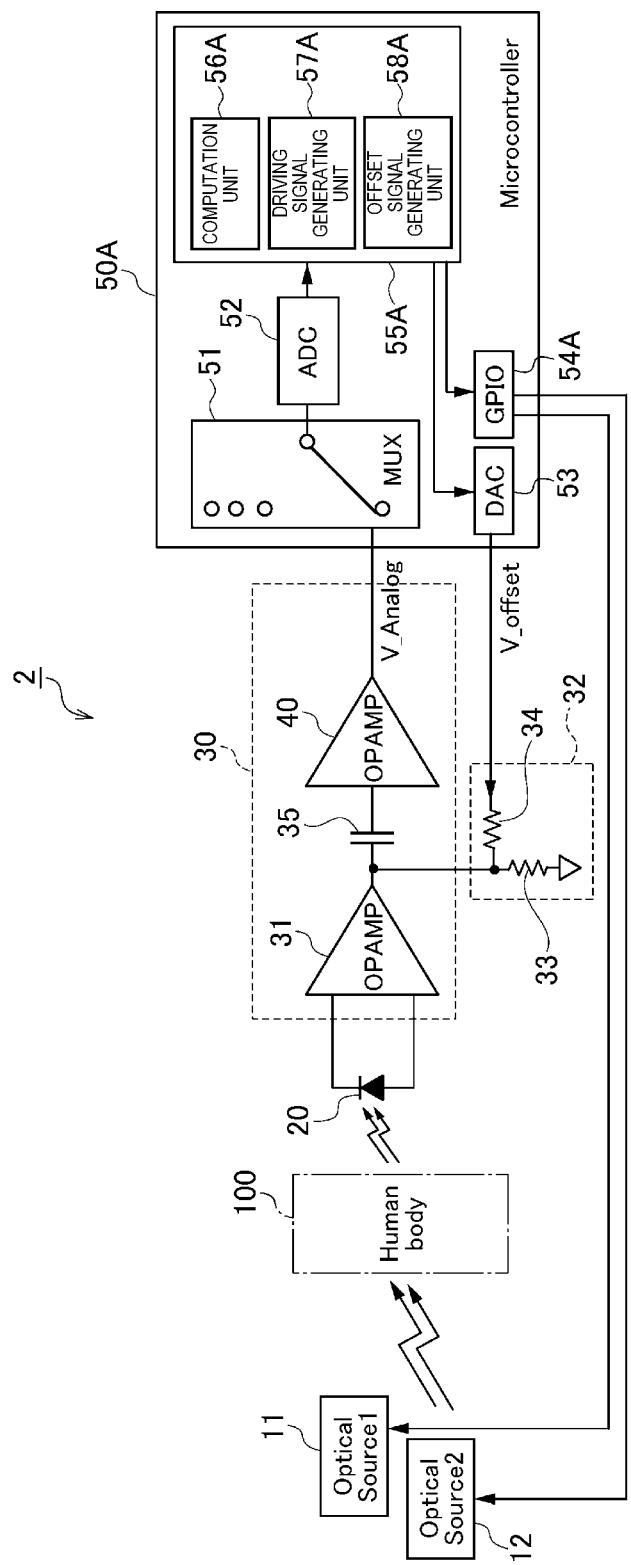
FIG. 7 is a block diagram illustrating the configuration of a biological sensor according to a second embodiment.

Next, the configuration of a biological sensor 2 according to a second embodiment will be described with reference to FIG. 7. Here, descriptions of configurations that are identical or similar to those in the biological sensor 1 according to the aforementioned first embodiment will be simplified or omitted, and primarily the points of difference will be described. FIG. 7 is a block diagram illustrating the configuration of the biological sensor 2 according to the second embodiment. In FIG. 7, constituent elements that are the same or equivalent to those in the first embodiment have been given the same reference numerals.

The biological sensor 2 differs from the aforementioned biological sensor 1 in that two light-emitting elements 11 and 12 are provided. The two light-emitting elements 11 and 12 emit respectively different wave lengths of light in order to obtain an abundance ratio between oxygenated hemoglobin and reduced hemoglobin, which indicates the blood oxygen saturation. For example, the one light-emitting element 11 emits near-infrared light whose absorption coefficient with respect to oxygenated hemoglobin is high (940 nm, for example). The other light-emitting element 12 emits near-red light whose absorption coefficient with respect to reduced hemoglobin is high (660 nm, for example).

A driving signal generating unit 57A that constitutes a microcontroller 50A generates pulse-form driving signals (pulse signals) having the same frequency (600 Hz, for example) but mutually different timings for the two light-emitting elements 11 and 12. The generated pulse signals having mutually different timings are outputted to the light-emitting element 11 and the light-emitting element 12 through an output port 54A.

Meanwhile, an offset signal generating unit 58A generates pulse-form offset signals (digital data), whose voltage values are adjusted independently from each other, in synchronization with the aforementioned driving signals (pulse signals). The generated offset signals (digital data) are converted into analog signals by the D/A converter 53, divided by the voltage dividing resistor group 32, and applied to the output terminal of the first operational amplifier 31.

A computation unit 56A computes an abundance ratio (absorbance ratio) between the oxygenated hemoglobin and the reduced hemoglobin from the detection signals of the respective wave lengths, and finds an oxygen saturation. The other configurations are the same or similar to those in the biological sensor 1, and thus detailed descriptions thereof will be omitted.

In the biological sensor 2 according to the exemplary embodiment, the driving signal generating unit 57A generates and outputs the pulse-form driving signals (pulse signals) having mutually different timings. Pulsed light having different wave lengths is then outputted from the two light-emitting elements 11 and 12 at respectively different timings. The pulsed light that is emitted from the light-emitting elements 11 and 12 and that passes through the human body 100 such as a fingertip or is reflected by the human body 100 is then received by the light-receiving element 20 and converted into the current detection signal.

Meanwhile, the offset signal generating unit 58A generates and outputs the pulse-form offset voltages (digital data), whose voltage values are adjusted independently from each other, in synchronization with both driving signals (pulse signals). The offset voltage is converted into an analog voltage by the D/A converter 53 and is applied to the voltage dividing resistor group 32. Accordingly, the voltage (offset voltage) obtained by the voltage division in accordance with the ratio between the resistance value of the first resistor 33 and the resistance value of the second resistor 34 that constitute the voltage dividing resistor group 32 is applied to the output terminal of the first operational amplifier 31 that constitutes the amplifying unit 30.

The detection signal obtained from the photoelectric conversion performed by the light-receiving element 20 is amplified by the amplifying unit 30. At this time, the output potential of the first operational amplifier 31 is offset by the offset voltage. Accordingly, a DC noise component such as external light, appearing as a direct current component, that is combined with the detection signal, is cut. The signal to noise ratios of the detection signals for each instance of pulsed light outputted from the two light-emitting elements 11 and 12 at different wave lengths are improved as a result.

The voltage detection signals I-V converted and amplified by the first operational amplifier 31 are inputted into the microcontroller 50A after being further amplified by the subsequent second operational amplifier 40. The amplified detection signals inputted into the microcontroller 50A are supplied to the computation unit 56A through the multiplexer 51 and the A/D converter 52. The detection signals of each wave length are then processed by the computation unit 56A, and the biological information such as the oxygen saturation is obtained from the absorbance ratio for each wave length, for example.

According to the exemplary embodiment, the pulsed light outputted from the two light-emitting elements 11 and 12 can be received by the single light-receiving element 20. The DC noise component can be cut from each instance of the pulsed light outputted from the two light-emitting elements 11 and 12 at mutually different wave lengths. Accordingly, the signal to noise ratio can be improved for each instance of the pulsed light outputted from the two light-emitting elements 11 and 12. As a result, for example, the absorbance ratio for each wave length can be measured accurately, and the oxygen saturation can be detected with a higher degree of accuracy. Although the direct current component and alternating current component of a signal are necessary when calculating the absorbance ratio on the digital side, the direct current component experiences feedback operation by a DAC in the microcontroller and is dynamically cut, and thus the absorbance is calculated by calculating a conversion value for the original analog direct current component from the feedback amount of the DAC. For example, in the case where the offset voltage applied for DC noise removal is 80 mV, adding 0.08*G (V) to the direct current output voltage of the output signal makes it possible to specify the direct current component inputted to the sensor and calculate an accurate absorbance ratio.

Third Embodiment

Next, the configuration of a biological sensor 3 according to a third embodiment will be described with reference to FIG. 8. Here, descriptions of configurations that are identical or similar to those in the biological sensor 1 according to the aforementioned first embodiment will be simplified or omitted, and primarily the points of difference will be described.

Figure 8:
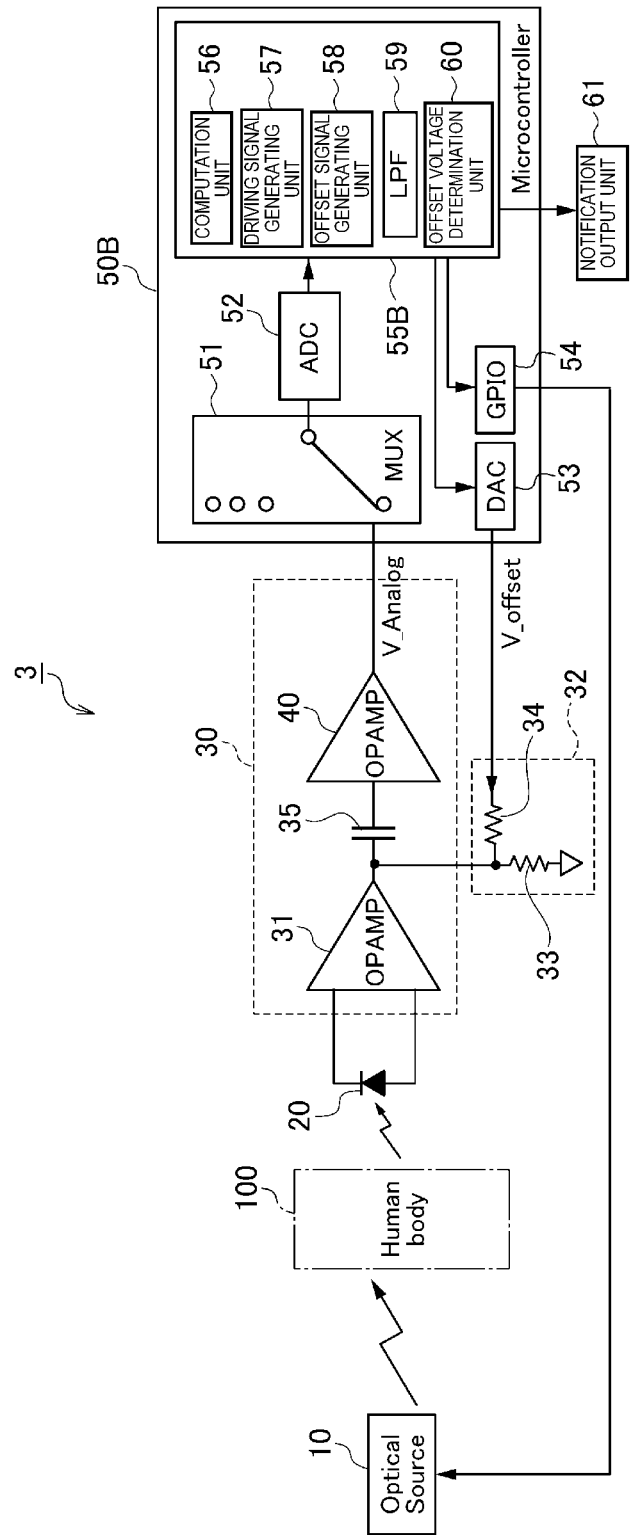
FIG. 8 is a block diagram illustrating the configuration of a biological sensor according to a third embodiment.

FIG. 8 is a block diagram illustrating the configuration of the biological sensor 3 according to the third embodiment. In FIG. 8, constituent elements that are the same or equivalent to those in the first embodiment have been given the same reference numerals.

A microcontroller 50B of the biological sensor 3 includes the multiplexer 51, the A/D converter 52, the D/A converter 53, the output port 54, and a CPU 55B, and the CPU 55B includes the computation unit 56, the driving signal generating unit 57, the offset signal generating unit 58, a low pass filter (LFP) 59, and an offset voltage determination unit 60. In other words, the CPU 55B of the microcontroller 50B differs from the CPU 55 of the microcontroller 50 according to the first embodiment in that the CPU 55B includes the LFP 59 and the offset voltage determination unit 60.

In the exemplary embodiment, the LFP 59 extracts a direct current component of the detection signal amplified by the amplifying unit 30, and the offset voltage determination unit 60 dynamically determines the offset voltage so that the direct current component extracted by the LFP 59 and a predetermined target value match. The LFP 59 functions as a direct current component extracting circuit as described herein, and the offset voltage determination unit 60 corresponds to an offset voltage determining circuit as described herein. In the case as the exemplary embodiment, where the configuration is such that the offset voltage is added to the output voltage from the first operational amplifier 31, the peak value of the offset voltage signal in the middle graph of FIG. 3 described above is dynamically controlled.

The LFP 59 is in the exemplary embodiment constituted by a low pass filter designed to have a cutoff frequency that is lower than a minimum measurable pulse frequency of 0.75 Hz (approximately 0.5 Hz, for example). By applying the LFP 59 to the detection signal from the amplifying unit 30, the voltage of a direct current component (base line) of an envelope connecting the peak values of each pulse that constitutes the detection signal is extracted.

The offset voltage determination unit 60 determines the offset voltage of the offset signal on the basis of the direct current component extracted by the LFP 59. Accordingly, the offset voltage determination unit 60 dynamically determines the offset voltage of the offset signal in accordance with changes in the detection signal from the amplifying unit 30. Specifically, the offset voltage determination unit 60 calculates a deviation of the direct current component extracted by the LFP 59 from the target value and controls the offset voltage so that the deviation decreases or eventually reaches zero. Here, the offset voltage control may be feedback control that successively performs feedback operation so that the stated deviation disappears, or may be feed-forward control that determines a prescribed offset voltage once (at the start of measurement, for example) on the basis of the stated deviation.

The offset signal generating unit 58 generates a pulse-form offset signal (digital data) having an amplitude based on the offset voltage determined by the offset voltage determination unit 60 and being synchronized with the pulse-form driving signal outputted by the driving signal generating unit 57. Like the first embodiment, the offset signal (digital data) generated by the offset signal generating unit 58 is converted into an analog signal by the D/A converter 53, outputted to the voltage dividing resistor group 32, and the value resulting from the voltage division is then applied to the output terminal of the first operational amplifier 31.

The detection voltage signal amplified by the first operational amplifier 31 and offset is inputted into the microcontroller 50B after being further amplified by the subsequent second operational amplifier 40. The detection signal inputted into the microcontroller 50B is supplied to the computation unit 56 through the multiplexer 51 and the A/D converter 52. The detection signal is then processed by the computation unit 56, and the biological information such as a pulse is obtained.

In addition, the offset voltage determination unit 60 determines whether or not the offset voltage control is within a control limit range and ends the measurement in the case where the offset voltage control is not within the control limit range. Here, "control limit" refers to a state in which the offset voltage control does not bring the deviation of the extracted direct current component from the target value below a predetermined value. For example, there are cases where the offset voltage control is outside the control limit range, such as the case where the light-receiving element 20 receives intense light such as sunlight, light from bright illumination, or the like. In the case where the offset voltage control is outside the control limit range, the offset voltage determination unit 60 stops the output of the driving signal by the driving signal generating unit 57 or stops the processing performed by the computation unit 56, and ends the measurement.

In addition, in the case where the offset voltage control is outside the control limit range, a notification output unit 61 may, in response to a command from the offset voltage determination unit 60, communicate error information indicating the end of measurement, a measurement failure, an inability to take a measurement, or the like to the user, along with the end of measurement or aside from the end of measurement. The notification output unit 61 may display the error information in a visual manner using an indicator constituted by a light emitter such as an LED, a liquid-crystal display, a control panel of the biological sensor 1, or the like; may output the error information as audio from a speaker; or may employ a combination thereof.

Figure 9:
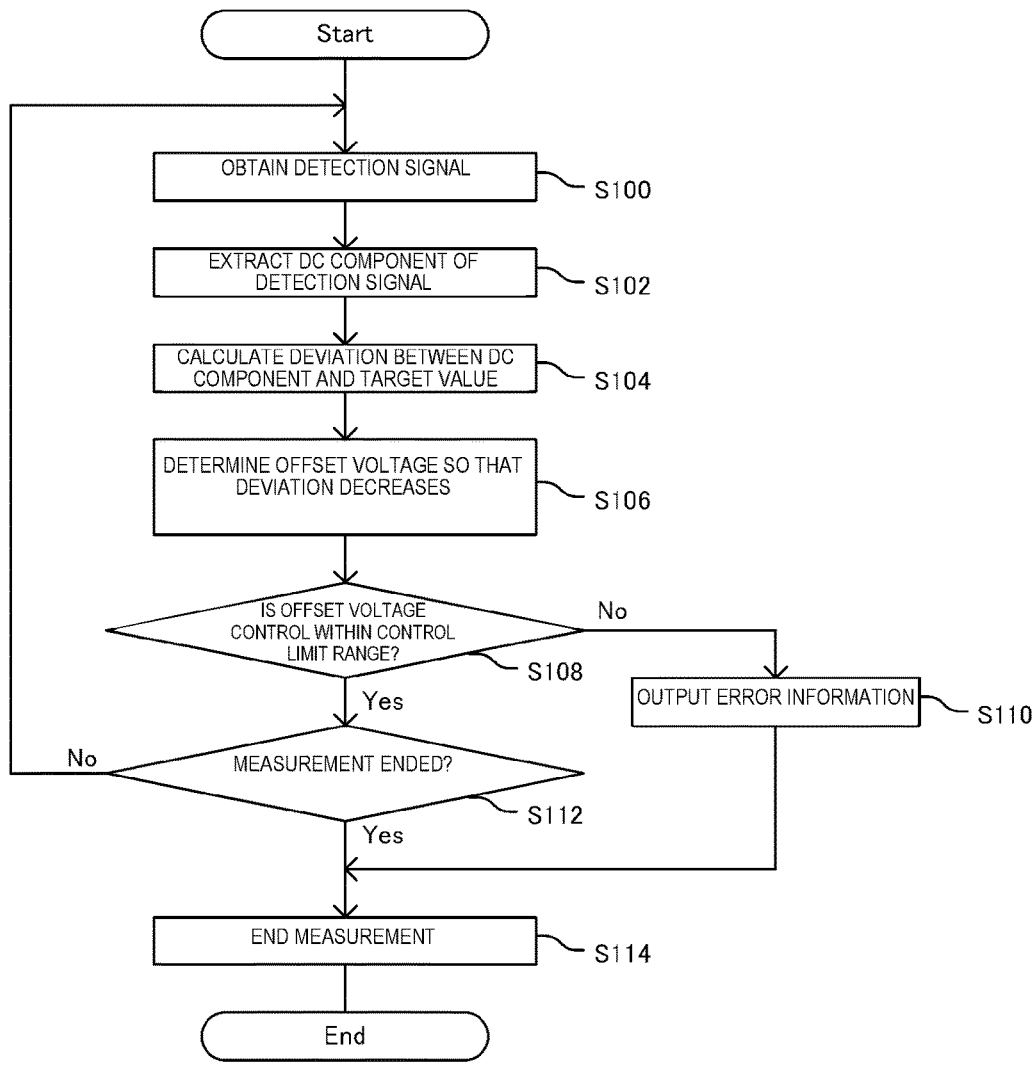
FIG. 9 is a flowchart illustrating operations performed by the biological sensor according to the third embodiment.

FIG. 9 is a flowchart illustrating operations performed by the biological sensor 3, that is, the microcontroller 50B in particular, according to the exemplary embodiment. In step S100, the detection signal from the amplifying unit 30 is obtained by the A/D converter 52. In step S102, the LFP 59 is applied to the detection signal and the direct current component of the detection signal is extracted.

In step S104, the offset voltage determination unit 60 calculates the deviation of the direct current component of the detection signal from the target value. In step S106, the offset voltage determination unit 60 controls the offset voltage so that the stated deviation decreases.

In step S108, the offset voltage determination unit 60 determines whether or not the offset voltage control is within the control limit range. In the case where the offset voltage control is outside the control limit range (step S108, No), in step S110, the offset voltage determination unit 60 causes the notification output unit 61 to output the error information, after which the process advances to step S114. In the case where the offset voltage control is within the control limit range (step S108, Yes), the measurement continues and the process advances to step S112.

In step S112, it is determined whether or not the measurement has ended. In the case where the measurement has not ended (step S112, No), the process returns to step S100. However, in the case where the measurement has ended (step S112, Yes), the process advances to step S114. In step S114, the offset voltage determination unit 60 ends the measurement by, for example, terminating the operations of one or both of the driving signal generating unit 57 and the computation unit 56.

According to the exemplary embodiment, the same high signal to noise ratio achieved in the first and second embodiments can be realized, and measurement robustness can be ensured by appropriately cutting the DC noise component even in the presence of variations caused by individual differences in the measurement subject's (subject's) skin state, thickness, diameter, and so on, seasonal changes in the skin state, differences in measurement areas, and so on, or fluctuations in signal levels due to body movement. Furthermore, the offset voltage range can be continually in use in a closed-loop circuit; as such, it is not necessary to set a gain margin in consideration of the stated variations or body movement, and the pulse and oxygen saturation measurement can consistently be carried out at the maximum gain setting.

Although embodiments of the present invention have been described thus far, the present invention is not intended to be limited to the aforementioned embodiments, and many variations can be carried out thereon. For example, although the voltage dividing resistor group 32 is connected in the path between the output terminal of the first operational amplifier 31 and the capacitor 35 in the aforementioned embodiments, the voltage dividing resistor group 32 may be connected in the path between the capacitor 35 and the input terminal of the second operational amplifier 40. However, in this case, it is necessary to provide a range sufficient to ensure that the first operational amplifier 31 is not saturated.

In addition, although the aforementioned embodiments describe configurations in which the amplifying unit 30 includes the operational amplifiers 31 and 40 in two stages, the configuration may be such that three or more stages of operational amplifiers are provided. In this case, the voltage dividing resistor group 32 may be connected in a path from the output terminal of a prescribed operational amplifier to the positive input terminal of the subsequent operational amplifier, and preferably, the voltage dividing resistor group 32 is connected in a path between the output terminal of the prescribed operational amplifier and a capacitor connected to the positive input terminal of the subsequent operational amplifier.

REFERENCE SIGNS LIST 1, 2, 3 biological sensor
10, 11, 12 light-emitting element
20 light-receiving element
30 amplifying unit
31 first operational amplifier
40 second operational amplifier
32 voltage dividing resistor group
35 capacitor
50, 50A, 50B microcontroller
53 D/A converter
54, 54A output port
55, 55A, 55B CPU
56, 56A computation unit
57, 57A driving signal generating unit
58, 58A offset signal generating unit
59 low pass filter (LPF)
60 offset voltage determination unit

The invention claimed is:
1. A biological sensor comprising:
a light-emitting element that emits light based on a driving signal;

a light-receiving element that outputs a current detection signal based on an intensity of received light including light emitted by the light-emitting element;

an amplifying circuit configured to convert the current detection signal into a voltage detection signal, amplify an alternating current component of the voltage detection signal, and output an amplified detection signal; and a microcontroller configured to:
generate the driving signal as a pulse-form driving signal, generate an offset signal as a pulse-form offset voltage that is synchronized with the pulse-form driving signal, apply the pulse-form offset voltage to an offset circuit coupled to the amplifying circuit to offset a direct current component of the voltage detection signal, and obtain biological information based on the amplified detection signal.

2. The biological sensor according to claim 1, wherein the amplifying circuit comprises:
a first operational amplifier that converts the current detection signal into the voltage detection signal;

a second operational amplifier that amplifies the voltage detection signal to output the amplified detection signal; and a capacitor connected between an output terminal of the first operational amplifier and an input terminal of the second operational amplifier.

3. The biological sensor according to claim 2, wherein the offset circuit is coupled to a path between the output terminal of the first operational amplifier and the input terminal of the second operational amplifier.

4. The biological sensor according to claim 3, wherein the offset circuit is coupled to a path between the output terminal of the first operational amplifier and the capacitor.

5. The biological sensor according to claim 1, wherein the offset circuit comprises a voltage dividing circuit that includes a plurality of resistors and that generates the offset voltage by voltage-dividing the offset signal generated by the microcontroller.

6. The biological sensor according to claim 1, further comprising a light-emitting element configured to output light of a different wave length from the light-emitting element, wherein the microcontroller is further configured to generate pulse-form driving signals having mutually different timings for each of the plurality of light-emitting elements, and to generate pulse-form offset voltages independent from each other in synchronization with the respective pulse-form driving signals outputted at mutually different timings.

7. The biological sensor according to claim 1, wherein the microcontroller is further configured to:
extract a direct current component of the amplified detection signal, and determine the offset voltage outputted by the offset circuit so that a deviation of the extracted direct current component from a target value decreases.

8. The biological sensor according to claim 7, wherein the microcontroller stops generating at least one of the driving signal and the offset signal when the deviation does not become less than or equal to a predetermined value as a result of the determined offset voltage.

* * * * *